United States Patent [19]

Waldmann et al.

[11] Patent Number: 5,502,167
[45] Date of Patent: Mar. 26, 1996

[54] CDR GRAFTED HUMANISED CHIMERIC T-CELL ANTIBODIES

[76] Inventors: Herman Waldmann, University of Cambridge, Department of Pathology, Immunology Div., Tennis Court Road; Louise Walsh, The University of Cambridge, Department of Pathology, Tennis Court Road, both of Cambridge, CB2 1QP; James S. Crowe; Alan P. Lewis, both of the Wellcome Foundation Limited, Langley Court, South Eden Park Road, Beckenham, Kent, BR3 3BS, all of Great Britain

[21] Appl. No.: 244,626

[22] PCT Filed: Dec. 4, 1992

[86] PCT No.: PCT/GB92/02251

§ 371 Date: Jun. 3, 1994

§ 102(e) Date: Jun. 3, 1994

[87] PCT Pub. No.: WO93/11237

PCT Pub. Date: Jun. 10, 1993

[30] Foreign Application Priority Data

Dec. 6, 1991 [GB] United Kingdom ............... 9125979

[51] Int. Cl.⁶ .................. A61K 35/16; A61K 39/00; A61K 39/395; C07K 16/00
[52] U.S. Cl. .................. 530/387.3; 435/69.1; 435/69.7; 435/91.1; 435/240.1; 435/240.27; 435/252.3; 435/320.1; 435/240.2; 530/387.1; 530/388.22; 530/388.75; 530/867; 536/23.53
[58] Field of Search .................. 435/69.1, 69.7, 435/91.1, 240.1, 240.2, 240.27, 252.3, 320.1; 530/387.1, 387.3, 388.22, 388.75, 867; 536/23.53

[56] References Cited

FOREIGN PATENT DOCUMENTS

| 0239400 | 9/1987 | European Pat. Off. | C07K 15/06 |
|---|---|---|---|
| 88/09344 | 12/1988 | WIPO | C07K 13/00 |
| 90/08187 | 7/1990 | WIPO | C12N 15/00 |
| 91/09968 | 7/1991 | WIPO | C12P 21/08 |
| 91/09967 | 7/1991 | WIPO | C12P 21/08 |
| 93/11237 | 6/1993 | WIPO | C12N 15/13 |

OTHER PUBLICATIONS

Uggla et al. Scand. J. Immunol. 29:507–515 (1989).
Yakida Hideo JP2097400 (1990) abstract only.
Chothia et al., J. Mol. Bio. 196:901–907 (1987).

Primary Examiner—Christina Y. Chan
Assistant Examiner—Donald E. Adams
Attorney, Agent, or Firm—Rothwell, Figg, Ernst & Kurz

[57] ABSTRACT

A humanised antibody is provided in which the amino acid sequence of the CDRs is derived from the sequence of CDRs of a monoclonal antibody having the specificity of binding to resting and activated T-cells, inhibiting T-cell proliferation and lysing T-cells from mice transgenic for human CD2 and in which sufficient of the amino acid sequence of each CDR has been retained to provide the same specificity for the humanised antibody.

6 Claims, 1 Drawing Sheet

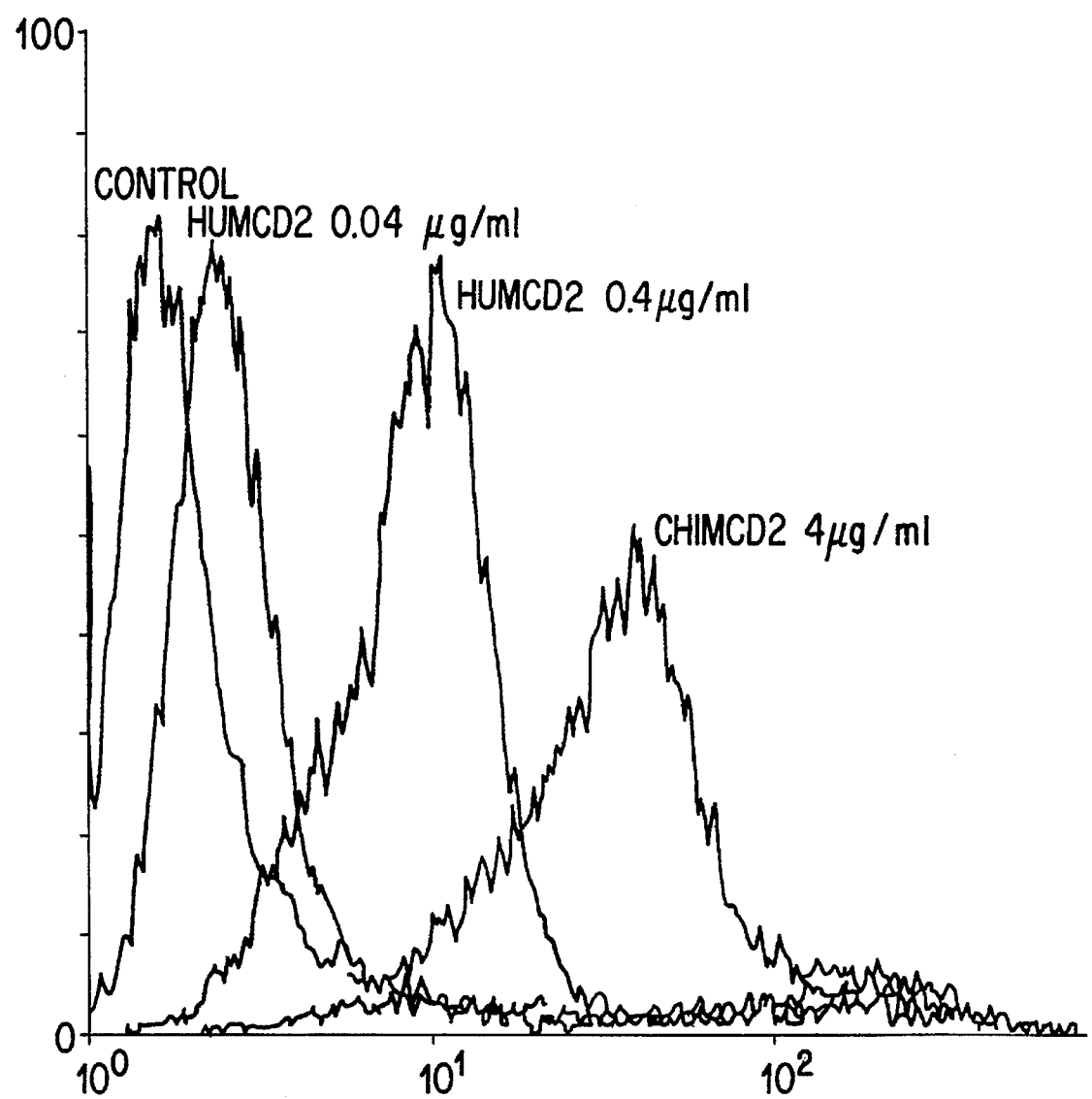

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 330 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..330

( x i ) SEQUENCE DESCRIPTION: SEQ ID NO:1:

```
GAT GTT GTG ATG ACA CAA ACT CCA GTC TCC CTG CCT GTC AGC CTT GGA         48
Asp Val Val Met Thr Gln Thr Pro Val Ser Leu Pro Val Ser Leu Gly
 1               5                  10                  15

GGT CAA GCC TCT ATC TCT TGC CGG TCA AGT CAG AGC CTG GTA CAC AGT         96
Gly Gln Ala Ser Ile Ser Cys Arg Ser Ser Gln Ser Leu Val His Ser
             20                  25                  30

AAT GGA AAC ACC TAC TTG CAT TGG TAC CTG CAG AAG CCA GGC CAG TCT        144
Asn Gly Asn Thr Tyr Leu His Trp Tyr Leu Gln Lys Pro Gly Gln Ser
         35                  40                  45

CCA CAG CTC CTC ATC TAT CGG GTT TCC AAC AGA TTT TCT GGG GTG CCA        192
Pro Gln Leu Leu Ile Tyr Arg Val Ser Asn Arg Phe Ser Gly Val Pro
     50                  55                  60

GAC AGG TTC AGT GGC AGT GGG TCA GGG ACA GAT TTC ACC CTC AAG ATC        240
Asp Arg Phe Ser Gly Ser Gly Ser Gly Thr Asp Phe Thr Leu Lys Ile
 65                  70                  75                  80

AGC AGA GTA GAG CCT GAG GAC TTG GGA GAT TAT TAC TGC TTA CAA AGT        288
Ser Arg Val Glu Pro Glu Asp Leu Gly Asp Tyr Tyr Cys Leu Gln Ser
                 85                  90                  95

ACA CAT TTT CCG TAC ACG TTT GGA GCT GGG ACC AAG CTG GAA                330
Thr His Phe Pro Tyr Thr Phe Gly Ala Gly Thr Lys Leu Glu
            100                 105                 110
```

( 2 ) INFORMATION FOR SEQ ID NO:2:

( i ) SEQUENCE CHARACTERISTICS:
        ( A ) LENGTH: 110 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Asp Val Val Met Thr Gln Thr Pro Val Ser Leu Pro Val Ser Leu Gly
 1               5                  10                  15

Gly Gln Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Gln Leu Leu Ile Tyr Arg Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Pro Glu Asp Leu Gly Asp Tyr Tyr Cys Leu Gln Ser
```

```
                            85                        90                         95
Thr  His  Phe  Pro  Tyr  Thr  Phe  Gly  Ala  Gly  Thr  Lys  Leu  Glu
                   100                      105                     110
```

( 2 ) INFORMATION FOR SEQ ID NO:3:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..48

( x i ) SEQUENCE DESCRIPTION: SEQ ID NO:3:

```
CGG  TCA  AGT  CAG  AGC  CTG  GTA  CAC  AGT  AAT  GGA  AAC  ACC  TAC  TTG  CAT    48
Arg  Ser  Ser  Gln  Ser  Leu  Val  His  Ser  Asn  Gly  Asn  Thr  Tyr  Leu  His
 1             5                        10                       15
```

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Arg  Ser  Ser  Gln  Ser  Leu  Val  His  Ser  Asn  Gly  Asn  Thr  Tyr  Leu  His
 1             5                        10                       15
```

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..21

( x i ) SEQUENCE DESCRIPTION: SEQ ID NO:5:

```
CGG  GTT  TCC  AAC  AGA  TTT  TCT                                                21
Arg  Val  Ser  Asn  Arg  Phe  Ser
 1             5
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Arg  Val  Ser  Asn  Arg  Phe  Ser
 1             5
```

( 2 ) INFORMATION FOR SEQ ID NO:7:

( i ) SEQUENCE CHARACTERISTICS:
( A ) LENGTH: 27 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 1..27

( x i ) SEQUENCE DESCRIPTION: SEQ ID NO:7:

| TTA | CAA | AGT | ACA | CAT | TTT | CCG | TAC | ACG | 27 |
|-----|-----|-----|-----|-----|-----|-----|-----|-----|----|
| Leu | Gln | Ser | Thr | His | Phe | Pro | Tyr | Thr | |
| 1   |     |     |     | 5   |     |     |     |     | |

( 2 ) INFORMATION FOR SEQ ID NO:8:

( i ) SEQUENCE CHARACTERISTICS:
( A ) LENGTH: 9 amino acids
( B ) TYPE: amino acid
( D ) TOPOLOGY: linear ( i i ) MOLECULE TYPE: protein ( x i ) SEQUENCE DESCRIPTION: SEQ ID NO:8:

Leu Gln Ser Thr His Phe Pro Tyr Thr
1               5

( 2 ) INFORMATION FOR SEQ ID NO:9:

( i ) SEQUENCE CHARACTERISTICS:
( A ) LENGTH: 297 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 1..297

( x i ) SEQUENCE DESCRIPTION: SEQ ID NO:9:

| GGA | GGT | TTG | GTG | AAA | CCT | GGG | GCT | TCT | CTG | AAA | CTC | TCT | TGT | GTA | GCC | 48 |
|-----|-----|-----|-----|-----|-----|-----|-----|-----|-----|-----|-----|-----|-----|-----|-----|----|
| Gly | Gly | Leu | Val | Lys | Pro | Gly | Ala | Ser | Leu | Lys | Leu | Ser | Cys | Val | Ala | |
| 1   |     |     |     | 5   |     |     |     |     | 10  |     |     |     |     | 15  |     | |

| TCG | GGA | TTC | ACT | TTC | AGT | GAC | TAC | TGG | ATG | AGC | TGG | GTT | CGC | CAG | ACT | 96 |
| Ser | Gly | Phe | Thr | Phe | Ser | Asp | Tyr | Trp | Met | Ser | Trp | Val | Arg | Gln | Thr | |
|     |     |     | 20  |     |     |     |     | 25  |     |     |     |     | 30  |     |     | |

| CCT | GGA | AAG | ACC | ATG | GAG | TGG | ATT | GGA | GAT | ATT | AAA | TAT | GAT | GGC | AGT | 144 |
| Pro | Gly | Lys | Thr | Met | Glu | Trp | Ile | Gly | Asp | Ile | Lys | Tyr | Asp | Gly | Ser | |
|     |     | 35  |     |     |     |     | 40  |     |     |     |     | 45  |     |     |     | |

| TAC | ACA | AAC | TAT | GCA | CCA | TCC | CTA | AAG | AAT | CGA | TTC | ACA | ATC | TCC | AGA | 192 |
| Tyr | Thr | Asn | Tyr | Ala | Pro | Ser | Leu | Lys | Asn | Arg | Phe | Thr | Ile | Ser | Arg | |
|     | 50  |     |     |     |     | 55  |     |     |     |     | 60  |     |     |     |     | |

| GAC | AAT | GCC | AAG | AGC | ACC | CTG | TAC | CTG | CAG | ATG | AGC | AAT | GTG | AGA | TCT | 240 |
| Asp | Asn | Ala | Lys | Ser | Thr | Leu | Tyr | Leu | Gln | Met | Ser | Asn | Val | Arg | Ser | |
| 65  |     |     |     |     | 70  |     |     |     |     | 75  |     |     |     |     | 80  | |

| GAG | GAC | ACA | GCC | ACT | TAT | TAC | TGT | ACT | AGA | GAG | GTA | CAA | CGG | AGT | TAC | 288 |
| Glu | Asp | Thr | Ala | Thr | Tyr | Tyr | Cys | Thr | Arg | Glu | Val | Gln | Arg | Ser | Tyr | |
|     |     |     |     | 85  |     |     |     |     | 90  |     |     |     |     | 95  |     | |

| TGG | GGC | CAA | 297 |
| Trp | Gly | Gln | |

( 2 ) INFORMATION FOR SEQ ID NO:10:

( i ) SEQUENCE CHARACTERISTICS:
  ( A ) LENGTH: 99 amino acids
  ( B ) TYPE: amino acid
  ( D ) TOPOLOGY: linear ( i i ) MOLECULE TYPE: protein ( x i ) SEQUENCE DESCRIPTION: SEQ ID NO:10:

| Gly | Gly | Leu | Val | Lys | Pro | Gly | Ala | Ser | Leu | Lys | Leu | Ser | Cys | Val | Ala |
|---|---|---|---|---|---|---|---|---|---|---|---|---|---|---|---|
| 1 | | | | 5 | | | | | 10 | | | | | 15 | |
| Ser | Gly | Phe | Thr | Phe | Ser | Asp | Tyr | Trp | Met | Ser | Trp | Val | Arg | Gln | Thr |
| | | | 20 | | | | | 25 | | | | | 30 | | |
| Pro | Gly | Lys | Thr | Met | Glu | Trp | Ile | Gly | Asp | Ile | Lys | Tyr | Asp | Gly | Ser |
| | | | 35 | | | | 40 | | | | | 45 | | | |
| Tyr | Thr | Asn | Tyr | Ala | Pro | Ser | Leu | Lys | Asn | Arg | Phe | Thr | Ile | Ser | Arg |
| | | 50 | | | | | 55 | | | | | 60 | | | |
| Asp | Asn | Ala | Lys | Ser | Thr | Leu | Tyr | Leu | Gln | Met | Ser | Asn | Val | Arg | Ser |
| 65 | | | | | 70 | | | | | 75 | | | | | 80 |
| Glu | Asp | Thr | Ala | Thr | Tyr | Tyr | Cys | Thr | Arg | Glu | Val | Gln | Arg | Ser | Tyr |
| | | | | 85 | | | | | 90 | | | | | 95 | |
| Trp | Gly | Gln |

( 2 ) INFORMATION FOR SEQ ID NO:11:

( i ) SEQUENCE CHARACTERISTICS:
    ( A ) LENGTH: 15 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 1..15

( x i ) SEQUENCE DESCRIPTION: SEQ ID NO:11:

```
GAC  TAC  TGG  ATG  AGC                                            15
Asp  Tyr  Trp  Met  Ser
 1                 5
```

( 2 ) INFORMATION FOR SEQ ID NO:12:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: protein ( x i ) SEQUENCE DESCRIPTION: SEQ ID NO:12:

Asp  Tyr  Trp  Met  Ser
 1                 5

( 2 ) INFORMATION FOR SEQ ID NO:13:

( i ) SEQUENCE CHARACTERISTICS:
    ( A ) LENGTH: 51 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 1..51

( x i ) SEQUENCE DESCRIPTION: SEQ ID NO:13:

| GAT | ATT | AAA | TAT | GAT | GGC | AGT | TAC | ACA | AAC | TAT | GCA | CCA | TCC | CTA | AAG | 48 |
| Asp | Ile | Lys | Tyr | Asp | Gly | Ser | Tyr | Thr | Asn | Tyr | Ala | Pro | Ser | Leu | Lys | |
| 1 | | | | 5 | | | | | 10 | | | | | 15 | | |

AAT                                                                                                          51
Asn ( 2 ) INFORMATION FOR SEQ ID NO:14:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Asp | Ile | Lys | Tyr | Asp | Gly | Ser | Tyr | Thr | Asn | Tyr | Ala | Pro | Ser | Leu | Lys |
| 1 | | | | 5 | | | | | 10 | | | | | 15 | |

Asn ( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..18

( x i ) SEQUENCE DESCRIPTION: SEQ ID NO:15:

| GAG | GTA | CAA | CGG | AGT | TAC | 18 |
| Glu | Val | Gln | Arg | Ser | Tyr | |
| 1 | | | | 5 | | |

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| Glu | Val | Gln | Arg | Ser | Tyr |
| 1 | | | | 5 | |

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

GATCAAGCTT CTCTACAGTT ACTGAGCACA                                              30

( 2 ) INFORMATION FOR SEQ ID NO:18:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:18:

CCATTACTGT GTACCAGGCT CTGACTTGAC CGACAGGAGA TGGAGGC    47

( 2 ) INFORMATION FOR SEQ ID NO:19:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

TGGTACACAG TAATGGAAAC ACCTACTTGC ATTGGTACCT GCAGAAG    47

( 2 ) INFORMATION FOR SEQ ID NO:20:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:20:

AGAAAATCTG TTGGAAACCC GATAGATCAG GAGCTG    36

( 2 ) INFORMATION FOR SEQ ID NO:21:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

CGGGTTTCCA ACAGATTTTC TGGGGTCCCT GACAGG    36

( 2 ) INFORMATION FOR SEQ ID NO:22:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:22:

CGTGTACGGA AAATGTGTAC TTTGTAAGCA GTAATAAACC CC    42

( 2 ) INFORMATION FOR SEQ ID NO:23:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:23:

TTACAAAGTA CACATTTTCC GTACACGTTC GGCGGAGGGA CC    42

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:24:

GATCAAGCTT CTAACACTCT CCCCTGTTGA    30

( 2 ) INFORMATION FOR SEQ ID NO:25:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:25:

TGGGATCGAT CAAGCTTTAC AGTTACTGAG C    31

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:26:

GCTCATCCAG TAGTCACTGA AGATGAATCC 30

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:27:

GACTACTGGA TGAGCTGGGT CCGCCAGGCT 30

(2) INFORMATION FOR SEQ ID NO:28:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:28:

TTAGTTTGTG TAACTGCCAT CATATTTAAT ATCTGCGACC CACTCCAG 48

(2) INFORMATION FOR SEQ ID NO:29:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:29:

GGCAGTTACA CAAACTATGC ACCATCCCTA AAGAATCGAT TCACTATCTC C 51

(2) INFORMATION FOR SEQ ID NO:30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:30:

GTAACTCCGT TGTACCTCTC TTGCACAGAA ATA  33

(2) INFORMATION FOR SEQ ID NO:31:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:31:

GAGGTACAAC GGAGTTACTG GGGCCAAGGG TCACTAGTCA CAGTCTCC  48

(2) INFORMATION FOR SEQ ID NO:32:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:32:

TAGAGTCCTG AGGGAATTCG GACAGCCGGG AAGGTG  36

(2) INFORMATION FOR SEQ ID NO:33:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

GCTGCTCCTT TTAAGCTTTG GGGTCAAGGC TCACTAGTCA CAGTCTCC  48

(2) INFORMATION FOR SEQ ID NO:34:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES ( x i ) SEQUENCE DESCRIPTION: SEQ ID NO:34:

AAGCTTCCGT CGAATTCATT TACCCGGAGA CAG    33

CDR GRAFTED HUMANISED CHIMERIC T-CELL ANTIBODIES

The present invention relates to a humanized antibody which binds to resting and activated T cells, inhibits T cell proliferation and lyses T cells from mice transgenic for human CD2, to the preparation of such an antibody and to a pharmaceutical composition which contains the antibody.

Antibodies typically comprise two heavy chains linked together by disulphide bonds and two light chains. Each light chain is linked to a respective heavy chain by disulphide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen.

The variable domains of each pair of light and heavy chains form the antigen binding site. The domains on the light and heavy chains have the same general structure and each domain comprises a framework of four regions, whose sequences are relatively conserved, connected by three complementarity determining regions (CDRs). The four framework regions largely adopt a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site. CDRs and framework regions of antibodies may be determined by reference to Kabat et al., ("Sequences of proteins of immunological interest" U.S. Dept. of Health and Human Services, U.S. Government Printing Office, 1987).

The preparation of an altered antibody in which the CDRs are derived from a different species than the framework of the antibody's variable domains is disclosed in EP-A-0239400. The CDRs may be derived from a rat or mouse monoclonal antibody. The framework of the variable domains, and the constant domains, of the altered antibody may be derived from a human antibody. Such a humanised antibody elicits a negligible immune response when administered to a human compared to the immune response mounted by a human against a rat or mouse antibody. Humanised CAMPATH-1 antibody (Campath is a Trademark of The Wellcome Foundation Ltd.) is disclosed in EP-A-0328404.

Human T cells play an important role in regulation of the immune response. Anti-T cell antibodies may therefore be immunosuppressive when administered in vivo. Such antibodies may be useful as a result in the treatment of for example, graft versus host disease, transplant rejection and autoimmune diseases such as rheumatoid arthritis.

Non-human monoclonal antibodies have been raised which are anti-T cell antibodies. However, non-human monoclonal antibodies do not fix human complement particularly well and are immunogenic when injected into a human patient. Chimaeric antibodies have been proposed in WO 89/09622 which are composed of a human constant region and a mouse variable region. However, a significant immunogenicity problem remains.

According to one aspect the present invention provides a humanised antibody in which the amino acid sequence of the CDRs is derived from the sequence of the CDRs of a monoclonal antibody having the specificity of binding to resting and activated T-cells, inhibiting T-cell proliferation and lysing T-cells from mice transgenic for human CD2 and in which sufficient of the amino acid sequence of each CDR has been retained to provide the same specificity for the humanised antibody.

According to another aspect of the present invention, there is provided a humanised antibody in which sufficient of the amino acid sequence of each CDR shown below is provided such that the antibody is capable of binding to a human T-cell antigen:

light chain:
  CDR1 (SEQ ID NOS: 3 and 4)
  CDR2 (SEQ ID NOS: 5 and 6)
  CDR3 (SEQ ID NOS: 7 and 8)
heavy chain:
  CDR1 (SEQ ID NOS: 11 and 12)
  CDR2 (SEQ ID NOS: 13 and 14)
  CDR3 (SEQ ID NOS: 15 and 16)

The antibody preferably has the structure of a natural antibody or a fragment thereof. The antibody may therefore comprise a complete antibody, a (Fab') 2 fragment, a Fab fragment, a light chain dimer or a heavy chain dimer. The antibody may be an IgG such as IgG1, IgG2, IgG3 or IgG4; or IgM, IgA, IgE or IgD. The constant domain of the antibody heavy chain may be selected accordingly. The light chain constant domain may be a kappa or lambda constant domain.

The antibody may be a chimaeric antibody of the type described in WO 86/01533. A chimaeric antibody according to WO 86/01533 comprises an antigen binding region and a non-immunoglobulin region. The antigen binding region is an antibody light chain variable domain and/or heavy chain variable domain. Typically the chimaeric antibody comprises both light and heavy chain variable domains. The non-immunoglobulin region is fused to the C-terminus of the antigen binding region. The non-immunoglobulin region is typically a non-immunoglobulin protein and may be an enzyme region, a region derived from a protein having known binding specificity, from a protein toxin or indeed from any protein expressed by a gene. The non-immunoglobulin region may be a carbohydrate region. The two regions of the chimaeric antibody may be connected via a cleavable linker sequence.

The light chain CDRs 1 to 3 and heavy chain CDRs 1 to 3 of Seq ID Nos: 3 to 8 and Seq ID Nos: 11 to 16 respectively are the CDRs of the anti-human T cell antibody YTH 655(5)6. YTH 655(5)6 is a rat IgG2b monoclonal antibody which binds to resting and activated T cells, inhibits T cell proliferation and lyses T cells from mice transgenic for human CD2. The specificity of a humanized YTH 655 antibody can be determined by its ability to bind to resting and activated T cells, inhibit T cell proliferation and lyse T cells from mice transgenic for human CD2.

Suitably, the CDRs of a humanised antibody are the light chain CDRs 1 to 3 and the heavy chain CDRs 1 to 3 above. The amino acid sequences of these CDRs may be changed, however. The amino acid sequence of these CDRs may be changed by up to 40% by amino acid substitutions, insertions and/or deletions, for example by up to 30%, up to 20% or up to 10%.

Each CDR may therefore include one or two amino acid substitutions, insertions and/or deletions. There may be up to three amino acid substitutions, insertions and/or deletions in light chain CDR3 or heavy chain CDR3. Up to four amino acid substitutions, insertions and/or deletions may be present in light chain CDR1. Up to six amino acid substitutions, insertions and/or deletions may be present, in heavy chain CDR2. Preferably the amino acid sequence of each CDR is substantially homologous to that of each CDR of the anti-T cell antibody YTH 655(5)6.

The framework and the constant domains of the antibody are human framework and human constant domains. Preferably the framework of the variable region of the antibody heavy chain is substantially homologous to the corresponding framework of the human protein KOL (Schmidt et al., Hoppe-Seyler's Z. Physiol. Chem., 364 713–747, 1983). Homology in respect of the framework is generally 80% or more with respect to KOL, for example 90% or more or 95% or more. A number of amino acid substitutions, insertions and/or deletions may be present. For example, the seventh residue of framework 4 is suitably Thr or Leu, preferably Leu. This residue is KOL residue 109 by Kabat et al., 1987. Other candidate framework changes that may be made to restore binding include amino acid residues 27, 30, 48, 66, 67, 71, 91, 93 and 94. The amino acid numbering is according to Kabat et al.

The framework of the variable region of the antibody light chain is typically substantially homologous to the variable domain framework of the protein HSIGKVII (EMBL data base: Klobeck, H. G., EMBL data library submitted 7th Apr., 1986). There is a frameshift in this sequence at position 452. To rectify the reading frame, a deletion of base 452(T) was made. Homology in respect of the framework is generally 80% or more with respect to HSIGKVII, for example 90% or more or 95% or more. A number of amino acid substitutions, insertions and/or deletions may be present, for example at amino acid residue 71 according to the numbering of Kabat et al.

A humanised antibody is prepared according to the invention by a process which comprises maintaining a host transformed with a first expression vector which encodes the light chain of the humanised antibody and with a second expression vector which encodes the heavy chain of the humanised antibody under such conditions that each chain is expressed and isolating the humanised antibody formed by assembly of the thus-expressed chains.

The first and second expression vectors may be the same vector. The invention further provides:

- a DNA sequence encoding the light chain or the heavy chain of the humanised antibody;
- an expression vector which incorporates said DNA sequence(s); and
- a host transformed with a said expression vector.

Each chain of the antibody may be prepared by CDR replacement. The CDRs of a variable region of a light or heavy chain of a human antibody are replaced by sufficient of the amino acid sequence of each CDR of the YTH 655 antibody that the resulting antibody is capable of binding to resting and activated T cells. The CDR-encoding regions of DNA encoding a hypervariable region of a human antibody chain are replaced by DNA encoding the desired CDRs. If appropriate, this altered DNA is linked to DNA encoding a constant domain for the antibody chain. The DNA is cloned into an expression vector. The expression vector is introduced into a compatible host cell which is cultured under such conditions that the antibody chain is expressed. Complementary antibody chains which are co-expressed in this way may then assembly to form the humanised antibody.

There are four general steps to humanise a monoclonal antibody. These are:

(1) determining the nucleotide and predicted amino acid sequence of the starting antibody light and heavy variable domains;

(2) designing the humanised antibody, i.e. deciding which antibody framework region to use during the humanising process;

(3) the actual humanising methodologies/techniques; and (4) the transfection and expression of the humanised antibody.

Step 1:
Determining the nucleotide and predicted amino acid sequence of the antibody light and heavy chain variable domains To humanise an antibody only the amino acid sequence of antibody's heavy and light chain variable domains needs to be known. The sequence of the constant domains is irrelevant because these do not contribute to the reshaping strategy. The simplest method of determining an antibody's variable domain amino acid sequence is from cloned cDNA encoding the heavy and light chain variable domain.

There are two general methods for cloning a given antibody's heavy and light chain variable domain cDNAs: (1) via a conventional cDNA library, or (2) via the polymerase chain reaction (PCR). Both of these methods are widely known. Given the nucleotide sequence of the cDNAs, it is a simple matter to translate this information into the predicted amino acid sequence of the antibody variable domains. In the present instance, the nucleotide sequence and predicted amino acid sequence of the rodent YTH 655 antibody chains are shown in SEQ ID NOS: 1 and 2 (light) and SEQ ID NOS: 9 and 10 (heavy).

Step 2:
Designing the humanised antibody

There are several factors to consider in deciding which human antibody sequence to use during the humanisation. The humanisation of light and heavy chains are considered independently of one another, but the reasoning is basically similar for each.

This selection process is based on the following rationale: A given antibody's antigen specificity and affinity is primarily determined by the amino acid sequence of the variable region CDRs. Variable domain framework residues have little or no direct contribution. The primary function of the framework regions is to hold the CDRs in their proper spatial orientation to recognize antigen. Thus the substitution of rodent CDRs into a human variable domain framework is most likely to result in retention of their correct spatial orientation if the human variable domain framework is highly homologous to the rodent variable domain from which they originated. A human variable domain should preferably be chosen therefore that is highly homologous to the rodent variable domain(s).

A suitable human antibody variable domain sequence can be selected as follows:

1. Using a computer program, search all available protein (and DNA) databases for those human antibody variable domain sequences that are most homologous to the rodent antibody variable domains. The output of a suitable program is a list of sequences most homologous to the rodent antibody, the percent homology to each sequence, and an alignment of each sequence to the rodent sequence. This is done independently for both the heavy and light chain variable domain sequences. The above analyses are more easily accomplished if only human immunoglobulin sequences are included.

2. List the human antibody variable domain sequences and compare for homology. Primarily the comparison is performed on length of CDRs, except CDR3 of the heavy chain which is quite variable. Human heavy chains and Kappa and Lambda light chains are divided into subgroups; Heavy chain 3 subgroups, Kappa chain 4 subgroups, Lambda chain 6 subgroups. The CDR sizes within each subgroup are similar but vary between subgroups. It is usually possible to match a rodent antibody CDR to one of the human subgroups as a first approximation of homology. Antibodies bearing CDRs of similar length are then compared for amino acid sequence homology, especially within the CDRs, but also in the surrounding framework regions. The human variable domain which is most homologous is chosen as the framework for humanisation.

Step 3:

The actual humanising methodologies/techniques

An antibody may be humanised by grafting the desired CDRs onto a human framework according to EP-A-0239400. A DNA sequence encoding the desired reshaped antibody can therefore be made beginning with the human DNA whose CDRs it is wished to reshape. The rodent variable domain amino acid sequence containing the desired CDRs is compared to that of the chosen human antibody variable domain sequence. The residues in the human variable domain are marked that need to be changed to the corresponding residue in the rodent to make the human variable region incorporate the rodent CDRs. There may also be residues that need substituting in, adding to or deleting from the human sequence.

Oligonucleotides are synthesized that can be used to mutagenize the human variable domain framework to contain the desired residues. Those oligonucleotides can be of any convenient size. One is normally only limited in length by the capabilities of the particular synthesizer one has available. The method of oligonucleotide-directed in vitro mutagenesis is well known.

Alternatively, humanisation may be achieved using the recombinant polymerase chain reaction (PCR) methodology of WO 92/07075. Using this methodology, a CDR may be spliced between the framework regions of a human antibody.

In general, the technique of UK Application No. 9022011.2 can be performed using a template comprising two human framework regions, AB and CD, and between them, the CDR which is to be replaced by a donor CDR. Primers A and B are used to amplify the framework region AB, and primers C and D used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanised product in a single reaction.

Step 4:

The transfection and expression of the reshaped antibody

Following the mutagenesis reactions to reshape the antibody, the mutagenised DNAs can be linked to an appropriate DNA encoding a light or heavy chain constant region, cloned into an expression vector, and transfected into host cells, preferably mammalian cells. These steps can be carried out in routine fashion. A reshaped antibody may therefore be prepared by a process comprising:

(a) preparing a first replicable expression vector including a suitable promoter operably linked to a DNA sequence which encodes at least a variable domain of an Ig heavy or light chain, the variable domain comprising framework regions from a human antibody and the CDRs required for the humanised antibody of the invention;

(b) preparing a second replicable expression vector including a suitable promoter operably linked to a DNA sequence which encodes at least the variable domain of a complementary Ig light or heavy chain respectively;

(c) transforming a cell line with the first or both prepared vectors; and (d) culturing said transformed cell line to produce said altered antibody.

Preferably the DNA sequence in step (a) encodes both the variable domain and the or each constant domain of the human antibody chain. The humanised antibody can be recovered and purified. The cell line which is transformed to produce the altered antibody may be a Chinese Hamster Ovary (CHO) cell line or an immortalised mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof.

Although the cell line used to produce the humanised antibody is preferably a mammalian cell line, any other suitable cell line, such as a bacterial cell line or a yeast cell line, may alternatively be used. For single antibody chains, it is envisaged that *E. coli*-derived bacterial strains could be used. The antibody obtained is checked for functionality. If functionality is lost, it is necessary to return to step (2) and alter the framework of the antibody.

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, generally, Scopes, R., *Protein Purification*, Springer-Verlag, N.Y. (1982)). Substantially pure immunoglobulins of at least about 90 to 95% homogeneity are preferred, and 98 to 99% or more homogeneity most preferred, for pharmaceutical uses. Once purified, partially or to homogeneity as desired, a humanised antibody may then be used therapeutically or in developing and performing assay procedures, immunofluorescent stainings, and the like (see, generally, *Immunological Methods*, Vols. I and II, Lefkovits and Pernis, eds., Academic Press, New York, N.Y. (1979 and 1981)).

The Human T cell antigen specific antibodies typically find use in treating a T-cell mediated disease state. Generally, where the cell linked to a disease has been identified as bearing the T cell antigen, then the humanised antibodies capable of binding the T cell antigen are suitable. For example, typical disease states suitable for treatment include graft versus host disease and transplant rejection in patients undergoing an organ transplant, such as heart, lungs, kidneys, liver, etc. Other diseases include autoimmune diseases, such as Type I diabetes, multiple sclerosis, rheumatoid arthritis, systemic lupus erythematosus, and myasthenia gravis.

The human-like antibodies of the present invention may also be used in combination with other antibodies, particularly human monoclonal antibodies reactive with other markers on cells responsible for the disease. For example, suitable T-cell markers can include those grouped into the so-called "Clusters of Differentiation," as named by the First International Leukocyte Differentiation Workshop, *Leukocyte Typing*, Bernard, et al., Eds., Springer-Verlag, N.Y. (1984).

The antibodies can also be used as separately administered compositions given in conjunction with chemotherapeutic or immunosuppressive agents. Typically, the agents will include cyclosporin A or a purine analog (e.g., methotrexate, 6-mercaptopurine, or the like), but numerous additional agents (e.g., cyclophosphamide, prednisone, etc.) well-known to those skilled in the art may also be utilized.

An antibody of the present invention may form part of an immunotoxin. Immunotoxins are characterized by two components and are particularly useful for killing selected cells in vitro or in vivo. One component is a cytotoxic agent which is usually fatal to a cell when attached or absorbed. The second component, known as the "delivery vehicle", provides a means for delivering the toxic agent to a particular cell type, such as cells comprising a carcinoma. The two components are commonly chemically bonded together by any of a variety of well-known chemical procedures. For example, when the cytotoxic agent is a protein and the second component is an intact immunoglobulin, the linkage may be by way of heterobifunctional cross-linkers, e.g., SPDP, carbodiimide, glutaraldehyde, or the like. Production of various immunotoxins is well-known with the art, and can be found, for example in "Monoclonal Antibody-Toxin Conjugates: Aiming the Magic Bullet", Thorpe et al., *Monoclonal Antibodies in Clinical Medicine*, Academic Press, pp. 168–190 (1982).

A variety of cytotoxic agents are suitable for use in immunotoxins. Cytotoxic agents can include radionuclides, such as Iodine-131, Yttrium-90, Rhenium-188, and Bismuth-212; a number of chemotherapeutic drugs, such as vindesine, methotrexate, adriamycin, and cisplatin; and cytotoxic proteins such as ribosomal inhibiting proteins like pokeweed antiviral protein, Pseudomonas exotoxin A, ricin, diphtheria toxin, ricin A chain, etc., or an agent active at the cell surface, such as the phospholipase enzymes (e.g., phospholipase C). See, generally, "Chimeric Toxins," Olsnes and Phil, *Pharmac. Ther.*, 25:335–381 (1982), and "Monoclonal Antibodies for Cancer Detection and Therapy," eds. Baldwin and Byers, pp. 159–179, 224–266, Academic Press (1985).

The delivery component of the immunotoxin is a humanised antibody according to the present invention. Intact immunoglobulins or their binding fragments, such as Fab, are preferably used. Typically, the antibodies in the immunotoxins will be of the human IgA, IgM or IgG isotype, but other mammalian constant regions may be utilized as desired.

The invention further provides a pharmaceutical composition comprising a pharmaceutially acceptable carrier or diluent and, as active ingredient, a humanised antibody according to the invention. The composition may be comprise an immunotoxin according to the invention. The humanised antibody, immunotoxin and pharmaceutical compositions thereof of this invention are particularly useful for parenteral administration, i.e., subcutaneously, intramuscularly or intravenously.

The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, *Remington's Pharmaceutical Science*, 15th ed., Mack Publishing Company, Easton, Pa. (1980).

The antibodies of this invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present human-like antibodies or a cocktail thereof can be administered for prophylactic and/or therapeutic treatments. In therapeutic application, compositions are administered to a patient already suffering from a disease, in an amount sufficient to cure or at least partially arrest or alleviate the disease and its complications. An amount adequate to accomplish this is defined as a "therapeutically effective dose." Amounts effective for this use will depend upon the severity of the infection and the general state of the patient's own immune system, but generally range from about 1 to about 200 mg of antibody per dose, with dosages of from 5 to 25 mg per patient being more commonly used. It must be kept in mind that the materials of the invention may generally be employed in serious disease states, that is life-threatening or potentially life-threatening situations. In such cases, in view of the minimization of extraneous substances and the lower probability of "foreign substance" rejections which are achieved by the present human-like antibodies of this invention, it is possible and may be felt desirable by the treating physician to administer substantial excesses of these antibodies.

In prophylactic applications, compositions containing the present antibodies or a cocktail thereof are administered to a patient not already in a disease state to enhance the patient's resistance. Such an amount is defined to be a "prophylactically effective dose". In this use, the precise amounts again depend upon the patient's state of health and general level of immunity, but generally range from 0.1 to 25 mg per dose, especially 0.5 to 2.5 mg per patient. A preferred prophylactic use is for the prevention of kidney transplant rejection.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

Human-like antibodies of the present invention can further find a wide variety of utilities in vitro. By way of example, the exemplary antibodies can be utilized for T-cell typing, for isolating specific YTH 655 antigen bearing cells or fragments of the receptor, for vaccine preparation, or the like.

For diagnostic purposes, the antibodies may either be labelled or unlabelled. Unlabelled antibodies can be used in combination with other labelled antibodies (second antibodies) that are reactive with the humanised antibody, such as antibodies specific for human immunoglobulin constant regions. Alternatively, the antibodies can be directly labelled. A wide variety of labels may be employed, such as radionuclides, fluors, enzymes, enzyme substrates, enzyme cofactors, enzyme inhibitors, ligands (particularly haptens), etc. Numerous types of immunoassays are available and are well known to those skilled in the art.

Kits can also be supplied for use with the subject antibodies in the protection against or detection of a cellular activity or for the presence of a selected antigen. Thus, a humanised antibody of the present invention may be provided, usually in a lyophilized form in a container, either alone or in conjunction with additional antibodies specific for the desired cell type. The antibodies, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the chimeric antibody is employed in an assay, this will usually be present in a separate vial. The second antibody is typically conjugated to a label and formulated in an analogous manner with the antibody formulations described above.

FIG. 1.

Binding of Humanized YTH 655 to MF14 cells.

The activity of humanized YTH 655 (HUMCD2) was assayed by FACS using an activated T cell line called MF14. A chimeric YTH 655 (CHIMCD2) containing a human IgG1 constant region and YTH 655 variable regions was used as a control. Cells were first incubated with either chimeric YTH 655 or humanized YTH 655. After washing, the cells were incubated with a commercially available anti-human FITC then analyzed by FACS. The figure shows that the binding of humanized YTH 655 is equivalent to binding of chimeric YTH 655 and that the humanized YTH 655 binding can be titrated. The antigen specificity of the humanized monoclonal antibody, therefore, has been retained.

The following Example illustrates the invention.

Cloning and Sequencing of YTH 655 antibody heavy chain

A cDNA encoding the VH region of the YTH 655 antibody was isolated by a polymerase chain reaction (PCR)-based method (Orlandi et al., PNAS USA, 86: 3833–3837, 1989) with some modifications. Total RNA was isolated from hybridoma cells by the guanidine thiocyanate method (Chirgwin et al., Biochemistry, 18: 5294, 1979), and poly (A)⁻ RNA was isolated by passage of total RNA through, and elution from a poly (U) sepharose 4B column (Pharmacia, Milton Keynes, U.K.). For first strand synthesis, 5 ug poly (A)⁻ RNA was combined with 250 uM each dNTP, 10 mM dithiothreitol, 50 mM Tris.HCl (pH8.2 at 42° C.), 10 mM MgCl12, 100 mM KCl, 10 pmoles of the $V_H$ region-specific primer VH₁FOR[5'-d(TGA GGA GAC GGT GAC CGT GGT CCC TTG GCC CCA G] and diethyl pyrocarbonate (DEPC)—treated distilled water to 24 ul. This was heated to 70° C. for 10 minutes, then 42° C. for 10 minutes before adding 23 units Super RT (AMV reverse transcriptase; Anglia Biotec, Colchester, UK). The reaction was carried out at 42° C. for 1 hour.

Subsequent 50 ul PCR amplifications consisted of 5 ul of the first strand synthesis reaction (unpurified), 500 uM each dNTP, 67 mM Tris-HC1 (pH8.8 at 25° C.), 17 mM (NH4)₂ SO., 10 mM MgCl₂, 20 ug/ml gelatin, 5 units TAQ DNA polymerase (Koch-Light, Haverhill, U.K.), 25 pmoles of primer VH₁FOR and 25 pmoles of the mixed primer VH₁BACK[5'-d(AGG T(CG) (CA) A(GA)CTGC AG(GC) AGT C(TA)G G]. Reactions were overlayed with mineral oil and subjected to 30 cycles of 1.5 minutes at 95° C. (denaturation), 3 minutes at 50° C. (annealing) and 3 minutes at 72° C. (extension) with a Techne PHC-1 programmable cyclic reactor. The final cycle contained a 10 minute extension time.

The sample was frozen at −20° C. and the mineral oil (a viscous liquid at −20° C.) was removed by aspiration. The aqueous phase was thawed and, after electrophoresis through 2% agarose, a 350 bp PCR product was gel-purified. The PCR product was double-digested with PstI and BstEII. Initially this was cloned into the PstI and BstEII restriction sites of the vector M13VH PCR1 (Orlandi et al., 1989). However, on sequencing resulting clones by the dideoxy chain termination method (Sanger et al., PNAS USA 74: 5463–5467, (1977), the YTH 655 VH gene was found to contain an internal PstI restriction site situated in the framework region between CDR2 and CDR3. An alternative cloning procedure was undertaken whereby the PCR product was digested with PstI only and cloned into the PstI site of M13mp18 (Yanisch-Perron et al., Gene 33, 103–119, 1985). The complete VH gene was subsequently reconstructed by isolating the PstI fragment from M13mp18 and cloning it into the PstI site of M13VHPCR1 (containing the VH PstI-BstEII fragment). The correct orientation of the PstI fragment was determined by dideoxy sequence analysis. Finally, to ensure that the YTH 655 VH gene contains only one internal Pst1 site (i.e. that no DNA had been lost as a consequence of the step-wise cloning procedure) a 60 bp fragment encompassing this site was cloned and sequenced. The 60 bp fragment was generated by XmnI-BglII double digestion of the VH PCR product and was then cloned into the HincII-BamHI sites, respectively, of M13mp19.

Nucleotide sequence analysis of random VH PCR products from independent PCR amplifications, and independent RNA isolations, revealed a single species of VH region cDNA. The cDNA sequence and the predicted amino-acid sequence are shown below. As no additional VH region-encoding clones were found, it was assumed that this sequence was derived from the YTH 655 antibody gene.

Cloning and Sequencing of YTH 655 antibody light chain

Total RNA was isolated from hybridoma cells by the guanidine thiocyanate method (Chirguwin et al., Biochemistry, 18, 5294, 1979). Dynabeads Oligo (dT)₂₅ (Dynal) was used to extract mRNA from total RNA employing the manufacturer's protocol.

cDNA was synthesised from the isolated mRNA and cloned into the plasmid pSPORT-1 using the Superscript Plasmid System for cDNA Synthesis and Plasmid Cloning kit (BRL) following the method recommended by the manufacturer. *Eschericia coli*, Max Efficiency DH5α Competent Cells (BRL) were transformed with the resulting cDNA/pSPORT-1 ligation. Approximately 5000 colonies were lifted onto Hybond-N nylon filters (Amersham) and lysed, denatured and fixed following the method of Buluwela et al., (Nucleic Acids Res. 17, 452, 1989). The filters were treated with proteinase K (50 μg/ml) in 0.2×SSC, 0.1% SDS at 55° C. for 30 minutes and then excess debris removed with a tissue.

M13 phage supernatant with truncated light chain was used to make a probe to screen the filters. The M13 phage supernatant was PCR'd using M13 reverse and universal primers and 2 μl of $^{32}\alpha$ P-ATP. The filters were screened using 25 μl of the radioactive probe in the hybridization solution according to the method of Church and Gilbert (PNAS, 81, 1991–1995, 1982). Approximately 30 potential positive colonies were detected. Plasmid DNA was prepared from the positive clones by the method of Del Sal et al., (Nucleic Acids Research 16, 9878, 1988). The DNA was restricted with Not I and Sal I then analysed by Southern blot using the $^{32}P$ M13 phage supernatant probe previously described. Four positive clones were sequenced using T7, T3 and framework 4 primers following the dideoxy chain termination method (Sanger et al., PNAS, USA, 74, 5463–5467, 1977). Three clones were truncated and one was full length YTH 655 antibody light chain. The full length clone was sequenced fully using the dideoxy chain termination method.

Designing the chimaeric antibody

Using the selection procedure described in Step 2 above, the human variable domain frameworks of the KOL heavy chain (Kabat et al., 1987) and HSIGKVII light chain (EMBL data base; Klobeck, H. G. EMBL data library submitted 7th Apr., 1986) were chosen for the humanisation process.

Construction of the humanised heavy and light chain genes

The humanised heavy and light chains were constructed following the method of Lewis and Crowe (Gene 101, 297–302, 1991).

(i) Light Chain

Light chain oligonucleotide primers:

$A_L$: SEQ ID NO: 17:
$B_L$: SEQ ID NO: 18:
$C_L$: SEQ ID NO: 19:
$D_L$: SEQ ID NO: 20:
$E_L$: SEQ ID NO: 21:
$F_L$: SEQ ID NO: 22:
$G_L$: SEQ ID NO: 23:
$H_L$: SEQ ID NO: 24:

PCR reactions (Saiki et al., Science 239, 487–491, 1988) were performed in a programmable heating block (Hybaid) using 20 rounds of temperature cycling (94° C. for 1 minute 30 seconds, 50° C. for 2 min, and 72° C. for 3 min) followed by a final 10 min step at 72° C. 800 ng of each primer, a specified amount of template, and 2.5 units of Taq polymerase (Perkin Elmer Cetus) were used in a final volume of 100 μl with the reaction buffer as recommended by the manufacturer.

The initial template for the PCR was previously humanized Hum DXC2 light chain, a human kappa light chain with HSIGKVII frameworks which had subsequently undergone site-directed mutagenesis to replace CDRL1, CDRL2, and CDRL3 with rat antidigoxin monoclonal antibody (DX48) CDRL1, CDRL2 and CDRL3.

Four primary PCR reactions were initially carried out, with 10 ng of template per reaction, using the primer pairs $A_L$ with $B_L$, $C_L$ with $D_L$, $E_L$ with $F_L$, and $G_L$ with $H_L$ respectively. The products of these PCR reactions, fragments $AB_L$, $CD_L$, $EF_L$ and $GH_L$ respectively, were purified using Prep-A-Gene (Bio-Rad) following the protocol recommended by the manufacturer. Fragments $AB_L$ with $CD_L$, and $EF_L$ with $GH_L$ were combined using a quarter of each purified product, and subjected to recombinant PCR reactions with primers $A_L$ plus $D_L$, and $E_L$ plus $H_L$ respectively. The products of these reactions, fragments $AD_L$ and $EH_L$, were purified as above, and a quarter of each combined in a recombinant PCR reaction using primers $A_L$ and $H_L$. The final humanised light chain recombinant PCR product, $AH_L$, was cloned into the HindIII site of pUC-18 ($BR_L$) following the method of Crowe et al., 1991, utilising the HindIII sites in primers $A_L$ and $H_L$. Plasmid isolates were sequenced by the dideoxy chain termination method, and clones of the correct sequence chosen.

(ii) Heavy Chain

Heavy chain oligonucleotide primers:

$A_H$: SEQ ID NO: 25:
$B_H$: SEQ ID NO: 26:
$C_H$: SEQ ID NO: 27:
$D_H$: SEQ ID NO: 28:
$E_H$: SEQ ID NO: 29:
$F_H$: SEQ ID NO: 30:
$G_H$: SEQ ID NO: 31:
$H_H$: SEQ ID NO: 32:

The initial template for the PCR was humanised anti-CD4 heavy chain (on KOL framework; WO 92/05274; Gorman et al., Proc. Natl. Acad. Sci. USA 88, 1991) subsequently converted from genomic to cDNA context. The rodent CDR's were grafted on to the template following the recombinant PCR method as described above, but using oligonucleotide primers $A_H$ to $H_H$. Oligonucleotides $A_H$ and $H_H$ were designed with HindIII and EcoRI sites respectively to enable initial cloning of the humanised variable region, and a SpeI site was introduced into the KOL framework 4 (FR4) region of oligonucleotide $G_H$ to facilitate subsequent cloning of the variable region with a suitable constant region of choice. The SpeI site altered the threonine residue at position 109 (numbering according to Kabat et al., 1987) of the humanised anti-CD4 heavy chain template (proline in KOL) to a leucine residue (four out of the six human heavy J-minigenes possess a leucine at this position; Kabat et al., 1987). The humanised heavy chain variable region recombinant PCR product was cloned into HindIII/EcoRI-cut pUC-18 ($BR_L$), and plasmid isolates of the correct sequence were chosen. The FR4 and c1 constant regions of the humanised anti-CD4 heavy chain were PCR cloned into pUC-18 ($BR_L$) using oligonucleotide primers $X_H$ (SEQ ID NO: 33) and $Y_H$ (SEQ ID NO: 34). Primer $X_H$ contains SpeI and HindIII sites, and $Y_H$ an EcoRI site. The HindIII and EcoRI sites were used to clone the PCR product into pUC-18, and plasmid isolates of the correct sequence were selected. The complete heavy chain was subsequently reconstituted from the humanised variable region and γ1 constant region clones using the engineered FR4 SpeI site.

Humanized YTH 655 heavy and light chains were cloned into a eukaryotic expression vector under human cytomegalovirus promoters and expressed transiently in COS cells at 200 ng/ml as determined by IgG ELISA. A stable cell line expressing humanised YTH 655 heavy and light chains was made by transfecting NSO cells with the same eukaryotic expression vector used for the COS cell transfections. Binding to YTH 655 and a chimeric YTH 655 containing human IgG1 constant region and YTH 655 variable region were shown by FACS analysis to bind an activated T cell line called MF14. Humanised YTH 655 [4 ug/mg] binding to MF14 cells was equivalent to binding of the rat YTH 655 [4 ug/ml] and chimeric YTH 655 [4 ug/ml] as determined by FACS (Weir D.M. 1985 Handbook of Experimental Immunology Vol 1 and 2 4th Ed-Blackwell Scientific Publication, Oxford). The antigen specificity of the humanized monoclonal antibody, therefore, has been retained. Binding of humanized YTH 655 to MF14 cells was shown to be concentration dependent by FACS analysis.

We claim:

1. A humanised antibody that specifically binds resting and activated T-cells, inhibits T-Cell proliferation and lyses T-cells from mice transgenic for human CD2, the heavy and light chain variable domains of said antibody are composed of framework and complementary determining regions, wherein light chain complementary determining region 1 has the amino acid sequence set forth in SEQ ID NOs. 3 or 4, light chain complementary determining region 2 has the amino acid sequence set forth in SEQ ID NOs. 5 or 6, light chain complementary determining region 3 has the amino acid sequence set forth in SEQ ID NOs. 7 or 8, heavy chain complementary determining region 1 has the amino acid sequence set forth in SEQ ID NOs. 11 or 12, heavy chain complementary determining region 2 has the amino acid sequence set forth in SEQ ID NOs. 13 or 14, and heavy chain complementary determining region 3 has the amino acid sequence set forth in SEQ ID NOs. 15 or 16.

2. An antibody according to claim 1, in which the framework region of the light chain variable domain is substantially homologous to the variable domain framework region of the protein HSIGKV11.

3. An antibody according to claim 1, in which the framework region of the heavy chain variable domain is substantially homologous to the variable domain framework region of the protein KOL.

4. A DNA sequence encoding the light chain or the heavy chain of the humanised antibody of claim 1.

5. An expression vector which incorporates a DNA sequence as claimed in claim 4.

6. A host cell transformed with an expression vector as claimed in claim 5.

* * * * *